(12) United States Patent
Slavtcheff et al.

US006926904B2

(10) Patent No.: US 6,926,904 B2
(45) Date of Patent: *Aug. 9, 2005

(54) COSMETIC PRODUCT WITH PROOF DEVICE

(75) Inventors: Craig Stephen Slavtcheff, Guilford, CT (US); Liam Anthony Murray, Monroe, CT (US); Josephine Telesca, Trumbull, CT (US); Robert Edward Gott, Norwalk, CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 542 days.

This patent is subject to a terminal disclaimer.

(21) Appl. No.: 10/022,457

(22) Filed: Oct. 29, 2001

(65) Prior Publication Data

US 2002/0182235 A1 Dec. 5, 2002

Related U.S. Application Data

(60) Provisional application No. 60/294,461, filed on May 30, 2001.

(51) Int. Cl.[7] .......................... A61K 9/00; A61L 15/16; A61F 13/00
(52) U.S. Cl. ...................... 424/448; 424/443; 424/449; 424/400
(58) Field of Search ................................ 424/443, 448, 424/449

(56) References Cited

U.S. PATENT DOCUMENTS

| | | | |
|---|---|---|---|
| 3,571,947 A | 3/1971 | Maddison et al. | |
| 3,906,933 A | 9/1975 | Tur et al. | |
| 4,190,056 A | 2/1980 | Tapper et al. | |
| 4,532,937 A | 8/1985 | Miller | |
| 4,569,358 A | 2/1986 | Gormley | |
| 4,981,145 A | 1/1991 | Goldstein | |
| 5,088,502 A | 2/1992 | Miller | |
| 5,094,248 A | 3/1992 | Kawam | |
| 5,119,828 A | 6/1992 | Miller | |
| 5,433,214 A | 7/1995 | Brehm et al. | |
| 5,589,178 A | 12/1996 | Aubert et al. | |
| 5,684,573 A | 11/1997 | Khazaka et al. | |
| 5,727,949 A | 3/1998 | Bar-Or et al. | |
| 5,991,433 A | 11/1999 | Osanai et al. | |
| 6,270,783 B1 * | 8/2001 | Slavtcheff et al. | 424/402 |
| 2001/0023327 A1 | 9/2001 | Hill | |
| 2003/0225345 A1 * | 12/2003 | Slavtcheff et al. | 600/572 |

FOREIGN PATENT DOCUMENTS

| | | |
|---|---|---|
| DE | 3725235 | 2/1989 |
| DE | 4337528 | 7/1995 |
| FR | 2/-63/743 | 6/1971 |
| FR | 2063743 | 6/1971 |
| FR | 2 821 541 | 3/2001 |
| GB | 2 284 154 | 5/1995 |
| JP | 2001275992 | 3/2000 |
| WO | 02/069802 | 9/2002 |

OTHER PUBLICATIONS

Am J Dermatopathol Dec. 9, 1987 (6):500.
Elizabeth Arden "Challenge" Packaging—2000.
VICHY Laboratories Diagnostic Discs—1999.
Oil of Olay® D–SQUAME Test Discs—1999.
Dove® D–SQUAME Test Discs—1998.
reflect.com Test Discs—1999.
Soap & Cosmetics, May 2001, "Sampling Innovations" by Marie Tillery, Associate Editor, pp. 29–32.
Book Excerpt: Canadian Living, Mar. 2001.

* cited by examiner

Primary Examiner—Thurman K. Page
Assistant Examiner—Isis Ghali
(74) Attorney, Agent, or Firm—Milton L. Honig

(57) ABSTRACT

A cosmetic product system is provided which includes a cosmetic composition for combating signs of aging, and a test device packaged with the composition. The device includes a mechanism for evaluating progress of the combat against the signs of aging occurring over a period of time within which the composition is applied to an area of skin being monitored.

7 Claims, 1 Drawing Sheet

COSMETIC PRODUCT WITH PROOF DEVICE

CROSS REFERENCE TO RELATED APPLICATIONS

Benefit is claimed to priority of Provisional Application Ser. No. 60/294,461 filed May 30, 2001.

BACKGROUND OF THE INVENTION

1. Field of the Invention

The invention concerns a cosmetic composition and method for combating the signs of aging in combination with a test device packaged with the composition to demonstrate proof of its efficacy.

2. The Related Art

A number of publications have disclosed test devices for the lay person to self-diagnose their skin conditions. U.S. Pat. No. 3,571,947 (Maddison et al.) discloses a system for identifying blemishes. A flexible, compliant film of plastic is imprinted with pictorials of various types of common blemishes. These reflect different dermal diseases. They are cross-referenced with a handbook identifying the diseases from the type of blemish. Cross-indexing treatments further provides a suggested treatment to remedy the medical condition.

U.S. Pat. No. 5,727,949 (Bar-Or et al.) provides a dual ring panel reference card. The panels are mounted for relative movement whereby a selected diagnostic characteristic of a skin problem can be aligned with a second diagnostic characteristic and a determinable prognosis revealed from the specific paired characteristics.

CuDerm Corporation has developed a simple diagnostic test to determine the degree of skin dryness. CuDerm utilizes adhesive discs (D-SQUAME) capable of removing a small section of squameous cells (skin cells) and compares the results against a chart. The disc is a transparent plastic with adhesive on one side. The test involves placing the adhesive surface of the disc against a user's forehead, peeling off the disc and placing same on a dark background card. Flakes from the skin stick to the adhesive surface and are visualized against the dark background. Other than loose flakes, no topographical imprint is ever taken from the evaluated user's skin.

There are many cosmetic products sold which advertise certain skin benefits. Consumers usually cannot easily discern whether the claimed benefit is actually delivered. Even if perceivable, these actives impart an effect which may emerge only slowly over a period of time. Anti-aging actives are particularly illustrative. Facial fine lines and wrinkles can be minimized with actives such as alpha hydroxycarboxlic acids and/or retinol, to provide some visible improvement over an extended application period. They don't function instantaneously.

Accordingly, it is an object of the present invention to provide a cosmetic product system and method whereby progress in treating the signs of aging with a cosmetic product is measured by a low cost simple test for a consumer to self evaluate efficacy of the product.

Another object of the present invention is to provide a cosmetic product system and method employing a low cost simple self evaluation tool for measuring changes in fine lines and wrinkles on the face or other aging susceptible parts of the human dermis.

SUMMARY OF THE INVENTION

A cosmetic product system is provided which includes:
(i) a cosmetic composition for combating signs of aging; and
(ii) a test device packaged with the composition, the device having a means for evaluating progress of the combat against the signs of aging over a period of time after the composition has been applied to an area of skin being monitored.

Among possible test devices are strips based on a water-insoluble substrate and a deformable semi-solid layer deposited onto the substrate, the layer being conformable to skin topography in three-dimension when placed against the monitored area of skin.

Alternatively the test device may include a water-insoluble substrate and an imaging layer deposited thereon, the layer being selectively sensitive to such skin properties as sebum concentration, moisture, temperature and pH.

Differentiation between facial ridge lines and depressions defining "wrinkles" also may be imaged through application of a powder, preferably a non-soluble substance respective to the adhesive layer of a test strip. Upon contact with the adhesive layer, only those raised areas of the skin topography will transfer powder. In this manner an image of fine lines and wrinkles appear as a powder pattern over the adhesive coating of the strip.

One aspect of the present invention requires a consumer to save the image for a period of time as a comparison against a subsequent test image. Testing may occur initially and thereafter at 4, 8, 12, 16 and/or 20 weeks. The time intervals and numbers may be longer or shorter. Therefore, it is desirable to fix the taken image to preserve same at least for a period of several weeks.

Fixatives will depend upon the particular test device. Those devices which image by deformation of an adhesive layer can utilize a transparent carrier substrate. Upon being printed with a wrinkle image, the adhesive surface is placed adjacent a darkened (e.g. black) area. The pattern can then be viewed through the transparent plastic supporting substrate.

Further fixation can occur by providing the darkened background area with a chemical interactive with the imaged adhesive layer. Hardening can then occur between the chemicals of the dark background and those of the adhesive. For instance, the reactions may be oxidation-reduction, acid-base or polymerization in nature.

Alternative fixation can occur with adhesives that are UV or even natural/fluorescent light sensitive. A light penetration preventive protective peel-off strip covers the light sensitive adhesive, the latter supported on a substrate sheet. In operation, the light protective sheet is removed, the adhesive surface applied to the treatment area of the face, an image is formed through deformation of the adhesive and then the resultant image is exposed to light which cures polymers forming the adhesive into a hardened material. Normally the supporting substrate bears a darkened color to contrast the image.

Another aspect of the present invention provides a system wherein a cosmetic composition is packaged with a test device. A variety of packaging arrangements are envisioned. The test device may be in the form of a cellulosic, plastic or combined material strip or tape placed into a carton alongside a container holding the cosmetic composition. Alternatively the test device may be incorporated as a panel segment of a carton, the latter protectively surrounding the cosmetic composition. In a variation thereof, the test device may be detachably joined to the package through a perforated or weakened construction line, or through an adhesive joinder.

Further, there is provided a method for evaluating efficacy of an anti-aging cosmetic product, the method including:

(A) providing a kit which includes:
  (i) a proof tape including a support substrate provided with an adhesive on a surface thereof, the adhesive having sufficient tack to maintain an imprint of fine lines and wrinkles after removal of the tape from the skin; and
  (ii) a fixative device for maintaining the imprint for a time longer than would occur without the fixative;
(B) applying the cosmetic product to the skin;
(C) placing the adhesive surface of the proof tape against the skin treated with the cosmetic product in step (B);
(D) removing the strip and contacting same with the fixative; and
(E) repeating steps (C) and (D) at a future time followed by comparison of patterns resultant from the first and second proof tape applications to the skin.

BRIEF DESCRIPTION OF THE DRAWINGS

Additional objects, features and benefits of the present invention will become more readily apparent from consideration of the drawing in which.

DETAILED DESCRIPTION OF THE INVENTION

Figure 1:
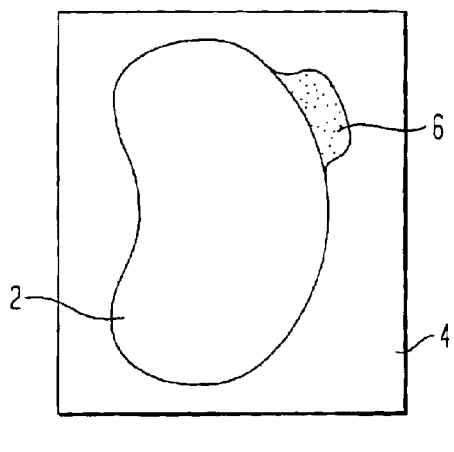
FIG. 1 is a first embodiment of an application strip according to the present invention.

Now consumers have been provided with a system for cosmetically combating the signs of aging in tandem with a test device for measuring progress on efficacy of the cosmetic composition over a prolonged period of its application. The cosmetic product system includes a cosmetic composition packaged together with a simple diagnostic test device.

Wrinkles are defined by peaks and troughs on the skin surface. Test devices according to the present invention transfer wrinkle topography into a 2D image so that a consumer can easily see where the wrinkles exist. Through this invention, elements of skin composition or state are utilized to "transfer" image of peaks/troughs onto a viewing substrate. Typical elements include surface squames, pH, oil/sebum concentration, moisture, temperature and direct 3D relief images. Generally these approaches involve a substrate, usually a water-insoluble cellulosic or plastic strip, coated with an imageable substance. Several possible embodiments of the test device are as follows:

(A) Surface Pretreatment

In this system, a strip is prepared as a water-insoluble substrate coated with an adhesive. Powder (e.g. titanium dioxide, talc or clay) is delivered onto a treatment area of skin. Thereafter, the adhesive side of the strip is applied over the powdered area. Removal after contact leaves an image (2D) of wrinkles. These strips are similar to transdermal patches utilized for drug delivery. They are available from Lohmann Therapie Systemes, Germany.

(B) pH

A litmus or other pH sensitive paper or plastic coated with a pH indicator is placed in contact with a skin treatment area. The pH produces a color change at point of contact. Since the peaks or ridges defining wrinkles first contact the pH sensitive paper, color change on the strip will be patterned according to that of the wrinkles.

(C) Oil/Sebum

Sebum sensitive film is available from the 3M Corporation. Low levels of mineral oil are dispersed on the film resulting in saturation wherever sebum is absorbed from peak areas on the skin surface. Colors darken along the sebum pattern thereby forming an image of the wrinkling.

(D) Moisture

A plastic or cellulosic strip is impregnated with a water activatable reagent causing a color change. Moisture from sweat along protruding areas of wrinkle formation attach to the strip when contacting the skin. Typical chemicals which can react with water to image include lactones or anhydrides opening to carboxylic acid, electrolytes activated by water dissolution closing an electric circuit or simply dissolution of water-soluble salts leaving an image in a background of undissolved salts.

(E) Temperature

A strip can be coated with a cholesteric crystal (liquid crystal) material which upon slight change of temperature caused by contact with skin temperature along ridges of the wrinkles changes from one to another color.

(F) Topography (Direct 3D Relief Images)

A supporting substrate sheet is provided with a tacky adhesive (e.g. polyacrylate, polyvinyl alcohol, alginate gums or starch), a wetted Plaster of Paris (e.g. Gypsona Plaster Bandage), or semi-solid wax (e.g. paraffin or microcrystalline polyethylene wax). Employment of a direct 3D relief image such as through use of an adhesive operates best when meeting four criteria. The adhesive should not hurt when pulled apart from the skin. Secondly, the adhesive needs to be sufficiently flowable (impressionable) to accept an image yet sufficiently non-flowable to retain the image once received. Thirdly, the system needs to be contrastable against a background. Finally, a support or substrate is required as a carrier.

Advantageously, a fixative is useful for maintaining a developed image of a wrinkle for a sustained period of time. Fixation can be chemical in nature. For instance, adhesives can be blended with UV or natural light or fluorescent sensitive activatable monomers or oligomers. Light is shielded from the adhesive by an opaque strip covering the curable adhesive surface. Once the adhesive has contacted the skin and formed a wrinkle pattern, the pattern is exposed to UV or natural or fluorescent light to harden the impression.

Another fixative system employs a transparent or darkened attachment strip. Here an adhesive deposited onto a blackened substrate is contacted against the target skin. Upon removal, the adhesive surface with its image is overlain with a transparent sheet. The latter fixes the image against destruction. In the alternative, the original substrate carrying the un-imaged adhesive can be transparent. After contact of adhesive with the target skin, the adhesive is removed and a black-surfaced strip is applied over the wrinkle image. Viewing of the resultant fixed pattern can then be through the original transparent substrate. This system is described in more detail below.

FIG. 1 illustrates a transparent strip 2 adhesively attached to a release backing 4. Strip 2 is kidney-shaped for placement adjacent either the right or left eye so as to cover the periorbital canphus (crow's foot area). This curvilinear shape allows for maximum coverage around an outer corner of the eye.

A tab 6 is attached to the strip 2. The tab serves as a gripping structure. Separation of the strip from the release backing is facilitated by initiating removal at the tab. The opaque, preferably black coloration of the tab in contrast to the transparency of the strip signals to a user the difference of this area and cues the user to start lifting at that point.

Figure 2:
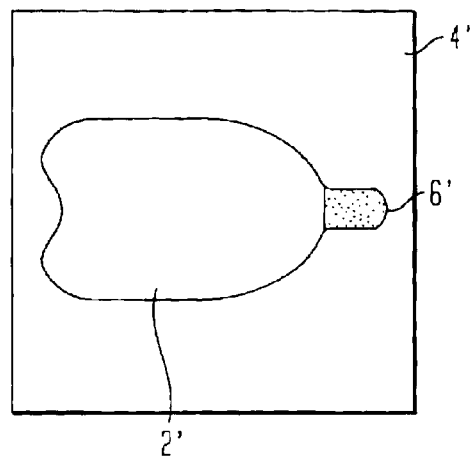
FIG. 2 is a second embodiment of an application strip according to the present invention.

FIG. 2 illustrates a second embodiment of a more elongate double lobed shape. Strip 2' is removably adhered onto a release backing 4'. Tab 6' is oriented between both lobes of the strip and lies along an axis of symmetry bisecting the strip. The elongate nature of this embodiment even more than the first embodiment ensures that eyebrow hairs are not trapped under the adhesive when applied. It is undesirable to capture hairs. Any hairs caught in the adhesive may cause pain upon the strip being removed. This is considered an undesirable ouch factor.

Figure 3:
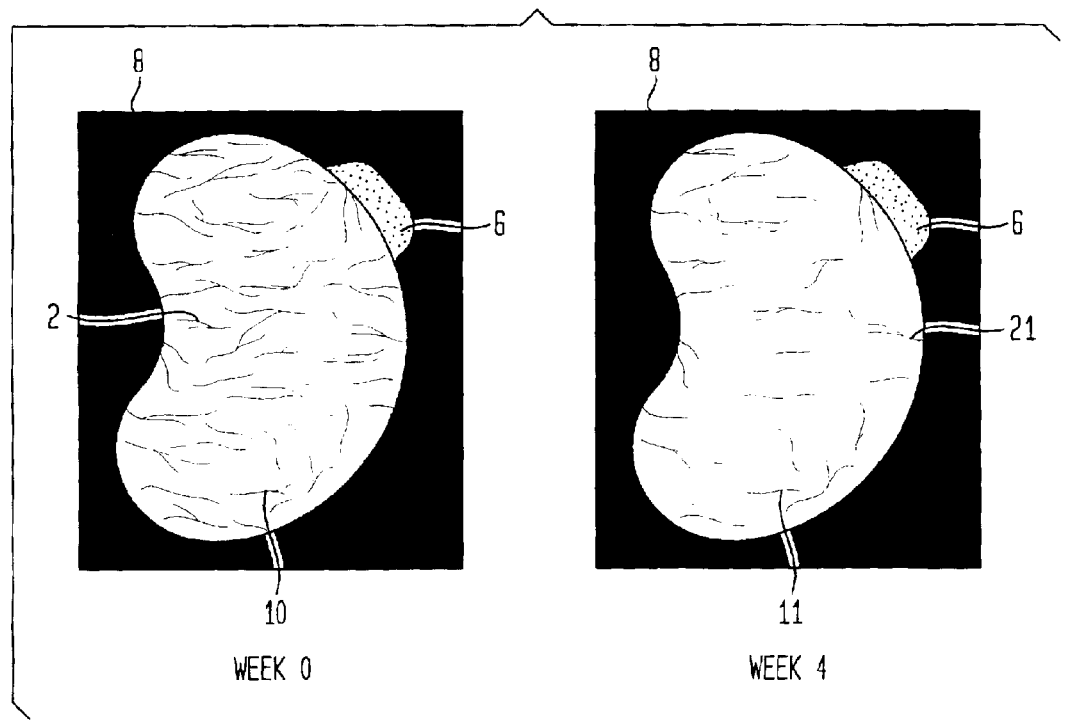
FIG. 3 is the application strip of the embodiment shown in FIG. 1 subsequent to being placed on the skin, removed therefrom and mounted on a darkened field reading card.

In the procedure for testing efficacy of various anti-aging products, the strip is removed from its release backing. Thereupon it is placed along an area of skin to be imaged for its topography. Facial areas are primarily intended for evaluation, and more particularly areas surrounding the eye. Subsequently, the strip is removed and placed upon an imaging card 8. The dark, preferably black background of the card fixes the imprint while the transparent strip allows a view of that imprint. FIG. 3 illustrates the strip showing fine lines and wrinkles 10 being visualized against the black background of the imaging card.

Subsequent to a baseline analysis of fine lines and wrinkles, treatment is begun with a selected cosmetic anti-aging product. Treatment is continued for a period of time sufficient to allow the product to treat the signs of aging.

A second imaging field is placed adjacent to the first. After the treatment period of time, such as four weeks, another imprint is taken by a second transparent strip 21. If the cosmetic product is properly functioning, fewer fine lines and wrinkles 11 will appear on the imaged second field. This procedure can then be repeated at six or eight weeks or at any further time interval. Each test will employ a fresh strip and new blackened area on the same or another image card.

With the particular illustrated embodiment, the adhesive is sufficiently mobile to flow into skin crevices representing the fine lines and wrinkles. Yet the adhesive is not too strong to minimize skin pull when removing the strip from the face. Without the appropriate flowability, only surface cells would be picked up without any imaging of the fine lines and wrinkles.

Strips for use with the illustrated embodiment will be transparent articles allowing observation of any patterns on a lower surface thereof. Suitable materials for the strip are plastics or cellulosics of any variety which can be formed as transparent films. Typically the plastic may be selected from polyethylene, polypropylene, polystyrene, polyester, polycarbonate, polyacrylate, polyvinyl chloride, polyvinyl alcohol and polybutene. Not only homopolymers but copolymers may be utilized for the strip material. Copolymers may be formed from such monomers as $C_2$–$C_{10}$ olefins, vinyl chloride, acrylates and styrene constructed through free-radical polymerization. Condensation plastics may also be utilized in the formation of copolymers wherein the monomers may be selected from $C_2$–$C_{10}$ dicarboxylic acids, $C_2$–$C_{10}$ polyols, $C_2$–$C_6$ alkoxylates and combinations thereof. Polyethylene, polypropylene and polyester terephthalate are the preferred plastic substrates for forming the strip.

The thickness of the strip may range anywhere from about 0.00001 to about 2 mm, preferably from about 0.0001 to about 1 mm, more preferably from about 0.001 to about 0.5 mm and optimally from about 0.01 to about 0.1 mm.

The backing is typically made from a material and in a manner that is generally impervious to the adhesive. The backing may be elastic or non-elastic but preferably the former. Flexibility allows easier removal of the adhesive strip. The backing can be formed from a variety of materials including organic polymers and cellulosics. A release coating such as a silicone may be placed on an upper surface of the backing to ease removal of the adjacent adhesive strip.

The adhesive may be a pressure sensitive or non-pressure sensitive type preferably as a layer with an average thickness from about 0.000005 mm to about 2 mm, preferably from about 0.00005 mm to about 0.5 mm, more preferably from about 0.0005 mm to about 0.25 mm, optimally from about 0.005 mm to about 0.05 mm.

Pressure sensitive adhesives suitable for use in this invention are coatable adhesives. A wide variety of coatable pressure sensitive adhesives can be used, such as solvent coatable, hot melt coatable, as well as latex PSA's that are coatable out of water. Also, solventless curable adhesives (often referred to as 100% solids) can be used. Where thicker adhesive coatings are desired, it may be desirable either to apply multiple layers of the adhesive, hot melt coat, or to photopolymerize the adhesive in situ. Specific examples of pressure sensitive adhesives include acrylates, such as isooctyl acrylate/acrylic acid copolymers, tackified acrylates, and plasticizer-containing acrylates such as those disclosed in U.S. Pat. No. 4,946,742 (Landin); natural or synthetic rubber resins, including thermoset rubbers as well as thermoplastic rubbers and elastomers, such as nitrile rubbers (e.g., acrylonitrile-butadiene), styrene-butadiene, styrene-isoprene, styrene-butadiene-styrene, styrene-isoprene-styrene, and natural rubber; silicone-based adhesives, such as polysiloxanes; polyolefins; polyesters; polyamides; and polyurethanes.

Particularly preferred are the acrylic type pressure sensitive adhesives. Most especially a pressure sensitive adhesive with a low tack value. These materials are commercially available under the FLEXCON brand.

Non-pressure sensitive adhesives are illustrated by polysaccharides. Examples are starches, chemically modified starches and natural or synthetic gums. Starches include corn and potato starches. Chemically modified starches include hydroxyalkylated starch, acylated starch, hydroxypropyl cellulose, hydroxypropyl methyl cellulose, ethyl cellulose and carboxymethyl cellulose. Gums include alginate, guar, carrageenan, agar, Karaya, pectin, gum arabic, sclerotium, gellatin and gum combinations.

Cosmetic compositions of the present invention can be denoted either as anti-aging or moisturizing compositions. These may be in the form of creams, lotions, pastes, sticks (e.g. lipsticks), or powders. These cosmetics normally will include a carrier. Suitable carriers include water, emollients (esters, hydrocarbons, silicones, polyols and mixtures thereof), emulsifiers, thickeners and combinations thereof. Most often the carrier will be an emulsion such as an oil-in-water or water-in-oil type. Amounts of the carrier may range from about 1 to about 99.9% by weight.

Anti-aging actives may include retinoids, ceramides, alpha or beta-hydroxycarboxylic acids, flavonoids, vitamins, sunscreens, anti-oxidants, preservatives and mixtures thereof.

Typical retinoids include retinol, retinoic acid and retinol esters. The latter include retinyl palmitate, retinyl linoleate, retinyl propionate, retinyl acetate and retinyl salicylate.

Alpha-hydroxy acids include the free acid, lactone and salt forms of glycolic acid, lactic acid, citric acid, gluconolactone, glucarolactone, tartaric acid, malic acid and mixtures thereof. Beta-hydroxycarboxylic acids are exemplified by salicylic acid as well as its esters (e.g. tridecylsalicylate) and salts including ammonium, alkanolammonium and alkalimetal salts.

Ceramides include Ceramide 1, Ceramide 2, Ceramide 3, Ceramide 3a, Ceramide 3b, Ceramide 4, Ceramide 5 and Ceramide 6, as well as pseudoceramides, phytosphingosines and tetraacetyl phytosphingosine.

Vitamins may include ascorbic acid as well as its water-soluble and water-insoluble derivatives. Illustrative are ascorbyl tetraisopalmitate, magnesium ascorbyl phosphate and ascorbyl glucoside. Other vitamins include Vitamin B3 (niacin, niacinamide and panthenol), biotin, folic acid, tocopherol and its esters (e.g. tocopherol isopalmitate), Vitamin D and combinations thereof.

Antioxidants include BHT (butylated hydroxytoluene), BHA (butylated hydroxyanisole), hydroquinone, ferulic acid and esters thereof, green tea extract, lipoic acid, N-acetyl cysteine, resveratrol and combinations thereof.

Amounts of the anti-aging actives may range anywhere from 0.0000001 to 30%, preferably from 0.0001 to 15%, more preferably from 0.1 to 5%, optimally from 0.5 to 2% by weight.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

All parts, percentages and proportions referred to herein and in the appended claims are by weight unless otherwise illustrated.

The foregoing description and examples illustrate selected embodiments of the present invention. In light thereof variations and modifications will be suggested to one skilled in the art, all of which are within the spirit and purview of this invention.

What is claimed is:

1. A method whereby a consumer can evaluate efficacy of an anti-aging cosmetic product, the method comprising:
    (A) providing to a consumer a kit which comprises:
        (i) a proof tape comprising a support substrate provided with an adhesive on a surface thereof, the adhesive having sufficient tack to maintain an imprint of fine lines and wrinkles after removal of the tape from the skin; and
        (ii) a fixative for maintaining the imprint for a time longer than would occur without the fixative;
    (B) applying the cosmetic product to the skin;
    (C) placing the adhesive surface of the proof tape against the skin treated with the cosmetic product in step (B);
    (D) removing the proof tape and contacting same with the fixative; and
    (E) repeating steps (C) and (D) at a future time with a second poof tape followed by comparison of patterns resultant from first and second proof tape applications to the skin.

2. The method according to claim 1 wherein the adhesive is a polymer selected from the group consisting of acrylates, starches, gums, polyvinyl alcohol and mixtures thereof.

3. The method according to claim 1 wherein the test device further comprises a protective cover substrate positioned over the adhesive, the cover substrate being removed prior to application of the adhesive against the area of skin being monitored.

4. The method according to claim 1 wherein the fixative is a material activated by UV or natural light that initiates polymerization hardening of the adhesive.

5. The method according to claim 1 wherein the support substrate comprises a material selected from a cellulosic, plastic or combination material, and the proof tape is placed into a carton alongside a container holding the cosmetic product.

6. The method according to claim 1 wherein the proof tape is incorporated as a panel segment of a carton protectively surrounding a container holding the cosmetic product.

7. The method according to claim 1 wherein the proof tape is detachably joined to a carton protectively surrounding a container holding the cosmetic product, joinder of the proof tape being through a means selected from the group consisting of perforations, weakened carton wall and adhesive joinder.

* * * * *